US012233386B2

(12) United States Patent
Schoefs et al.

(10) Patent No.: US 12,233,386 B2
(45) Date of Patent: Feb. 25, 2025

(54) IMPELLER GUARD

(71) Applicant: CYTIVA US LLC, Marlborough, MA (US)

(72) Inventors: Els E. N. Schoefs, Hoegarden (BE); Kurt Dreesen, Hoegarden (BE); Peter Dick Stedehouder, Medemblik (NL); Pieter De Conninck, Hoegarden (BE)

(73) Assignee: CYTIVA US LLC, Marlborough, MA (US)

( * ) Notice: Subject to any disclaimer, the term of this patent is extended or adjusted under 35 U.S.C. 154(b) by 796 days.

(21) Appl. No.: 17/495,598

(22) Filed: Oct. 6, 2021

(65) Prior Publication Data

US 2023/0106503 A1   Apr. 6, 2023

(51) Int. Cl.
*B01F 27/1132* (2022.01)
*B01F 27/808* (2022.01)

(52) U.S. Cl.
CPC ........ *B01F 27/1132* (2022.01); *B01F 27/808* (2022.01)

(58) Field of Classification Search
CPC ... B01F 27/1132; B01F 27/17; B01F 33/4535
See application file for complete search history.

(56) References Cited

U.S. PATENT DOCUMENTS

| | | | |
|---|---|---|---|
| 1,778,790 A * | 10/1930 | Brandl | F02M 1/00 48/189.4 |
| 5,758,965 A | 6/1998 | Gambrill et al. | |
| 5,865,539 A | 2/1999 | Rogers | |
| 6,881,033 B2 * | 4/2005 | Makinson | F04D 13/0606 417/423.12 |
| 7,740,401 B2 | 6/2010 | Kozlowski et al. | |
| 8,534,907 B2 * | 9/2013 | Yum | B01F 21/10 366/279 |
| 9,248,420 B2 | 2/2016 | Rawlings | |
| 9,550,157 B2 | 1/2017 | Erdenberger et al. | |
| 9,744,507 B2 | 8/2017 | Morrissey et al. | |
| 9,878,295 B2 | 1/2018 | Marshall | |
| 10,005,052 B2 | 6/2018 | Bernard et al. | |
| 10,610,839 B2 | 4/2020 | Morrissey et al. | |
| 2002/0112865 A1 * | 8/2002 | Murtagh | B01F 27/0725 7/114 |

(Continued)

FOREIGN PATENT DOCUMENTS

| | | |
|---|---|---|
| JP | 2015-536884 A | 12/2015 |
| JP | 2017-51947 A | 3/2017 |
| JP | 2020-116565 A | 8/2020 |

OTHER PUBLICATIONS

European Patent Office, Extended European Search Report issued in counterpart European Patent Application No. 22181662.2, mailed on Dec. 23, 2022.

(Continued)

*Primary Examiner* — Marc C Howell
*Assistant Examiner* — Patrick M McCarty
(74) *Attorney, Agent, or Firm* — Leydig, Voit & Mayer, Ltd.

(57) ABSTRACT

Guard for impellers, methods of using the guards, impeller assemblies including the guards mounted to impellers, impeller systems, and biocontainer systems including the impeller systems, are disclosed.

20 Claims, 15 Drawing Sheets

(56) References Cited

U.S. PATENT DOCUMENTS

| | | | |
|---|---|---|---|
| 2005/0135937 A1* | 6/2005 | Hardy | B01F 27/091 |
| | | | 416/204 R |
| 2010/0157725 A1* | 6/2010 | Terentiev | B01F 35/513 |
| | | | 366/331 |
| 2010/0220547 A1 | 9/2010 | Bernard et al. | |
| 2013/0003495 A1* | 1/2013 | Pyddoke | F04D 29/34 |
| | | | 366/343 |
| 2015/0117142 A1* | 4/2015 | Staheli | B01F 27/191 |
| | | | 366/279 |
| 2015/0259638 A1* | 9/2015 | Zeuch | B01F 35/513 |
| | | | 435/302.1 |
| 2015/0265986 A1* | 9/2015 | Cutting | B01F 35/31 |
| | | | 366/331 |
| 2018/0169595 A1* | 6/2018 | Mott | B01F 35/31 |
| 2020/0179885 A1 | 6/2020 | Sevenants et al. | |

OTHER PUBLICATIONS

Japanese Patent Office, Office Action issued in counterpart Japanese Patent Application No. 2022-107254, mailed on Jul. 4, 2023.

* cited by examiner

# IMPELLER GUARD

BACKGROUND OF THE INVENTION

The preparation of fluids, particularly solutions and suspensions in the pharmaceutical and biopharmaceutical industries, typically involves thorough mixing to provide the desired distribution of ingredients in the product. Many mixing operations are carried out in bioreactor bags with a mixing impeller mounted near the base of the vessel. A variety of impellers with different size impeller hubs, impeller blades and/or blade configurations can be used for mixing.

However, damage to the bioreactor bag can compromise the sterility of the fluid in the bag, leading to the loss of valuable fluid.

The present invention provides for ameliorating at least some of the disadvantages of the prior art. These and other advantages of the present invention will be apparent from the description as set forth below.

BRIEF SUMMARY OF THE INVENTION

An aspect of the invention provides a guard for an impeller having at least a first blade and a second blade, each of the first and second blades having front and rear blade faces, an upper edge, an outer edge, an upper outer corner where the upper edge contacts the outer edge, a lower edge, and an inner edge, the guard comprising: (A) an upper annular ring having an upper annular ring horizontal axis and a first internal diameter, the upper annular ring having an upper surface and a lower surface, wherein the lower surface includes at least a first blade receiving groove for receiving the upper outer corner of the first blade, the first blade receiving groove having first and second sides; and a second blade receiving groove for receiving the upper outer corner of the second blade, the second blade receiving groove having first and second sides; (B) a lower annular ring having a lower annular ring horizontal axis and a second internal diameter, wherein the second internal diameter is smaller than the first internal diameter; (C) at least a first brace member and a second brace member, each attached to the upper annular ring and the lower annular ring, each of the first brace member and second brace member being vertically arranged between the upper annular ring and the lower annular ring perpendicular to the upper annular ring horizontal axis and the lower annular ring horizontal axis, (1) the first brace member having a first brace member front wall, a first brace member rear wall, a first brace member outer side wall, and a first brace member inner side wall contacting the lower annular ring, the first brace member front wall or the first brace member rear wall being arranged to face a front or rear blade face of the first blade and forming the second side of the first blade receiving groove; (a) the first brace member having a vertical slot for receiving a portion of an inner edge of the first blade, and a catch for lockably receiving a portion of the lower edge of the first blade; (2) the second brace member having a second brace member front wall, a second brace member rear wall, a second brace member outer side wall and a second brace member inner side wall contacting the lower annular ring, the second brace member front wall or the second brace member rear wall being arranged to face a front or rear blade face of the second blade and forming the second side of the second blade receiving groove; (b) the second brace member having a vertical slot for receiving a portion of an inner edge of the second blade, and a catch for lockably receiving a portion of the lower edge of the second blade.

In another aspect, an impeller assembly is provided, comprising: an impeller having at least a first blade and a second blade, each of the first and second blades having front and rear blade faces, an upper edge, an outer edge, an upper outer corner where the upper edge contacts the outer edge, a lower edge, and an inner edge; and the guard according to an aspect of the invention, mounted to the impeller.

In yet another aspect, a method for mounting an aspect of the guard to an impeller is provided, the method comprising: positioning the inner edges of the blades of the impeller in the vertical slots of the respective brace members; positioning the upper outer corners of the blades of the impeller in the respective blade receiving grooves; and positioning the lower edges of the blades of the impeller in the catches of the respective brace members.

In yet another aspect, an impeller system is provided, comprising an aspect of the impeller assembly, a pin, and a seat fitment.

Another aspect relates to a biocontainer system, comprising: (a) a biocontainer comprising a closed container having an interior volume suitable for containing fluid, the container comprising a bottom wall, a top wall, at least one side wall, the side wall(s) being joined to the top wall and the bottom wall; and at least an inlet port, and a drain port, wherein the biocontainer further comprises: (b) an aspect of the impeller system, wherein the impeller is mounted to an inner surface of the bottom wall of the biocontainer.

BRIEF DESCRIPTION OF THE SEVERAL VIEWS OF THE DRAWING(S)

Figure 5A:
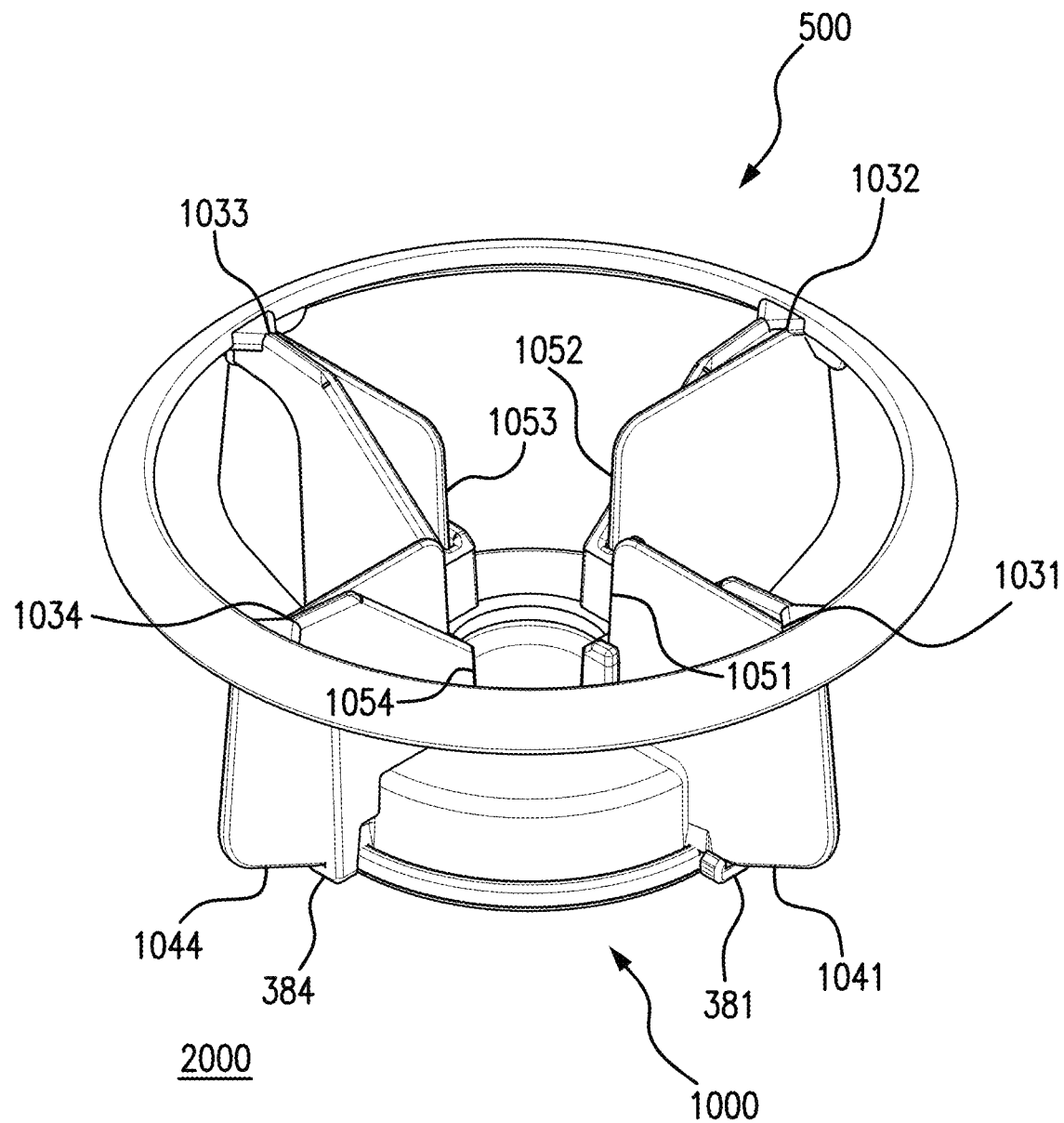
FIGS. 5A and 5B are, respectively, a top perspective view, and a top view, of an impeller assembly according to an aspect of the invention, comprising the guard as shown in FIG. 1A mounted to the impeller shown in FIG. 4.
Figure 6A:
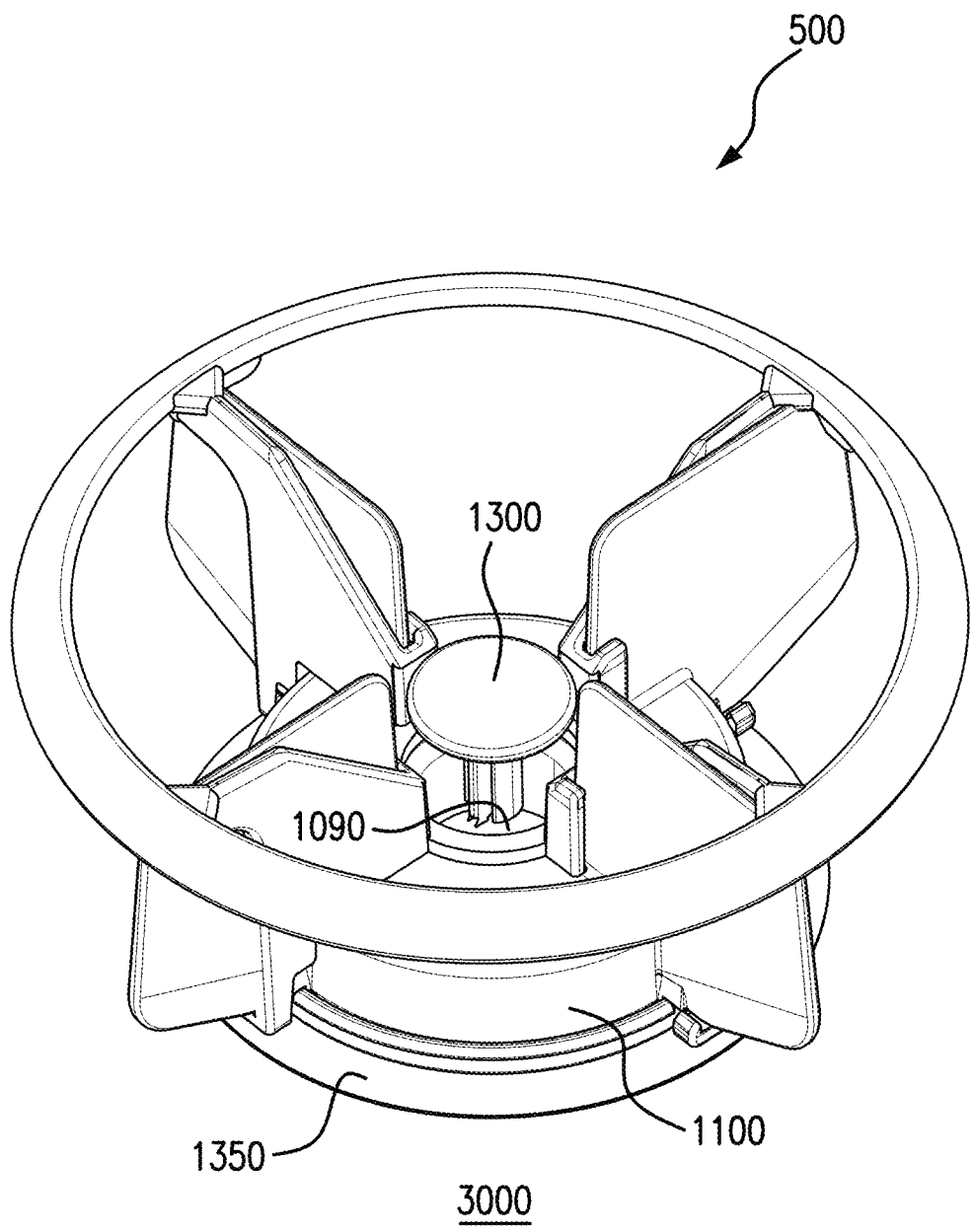
Figure 6B:
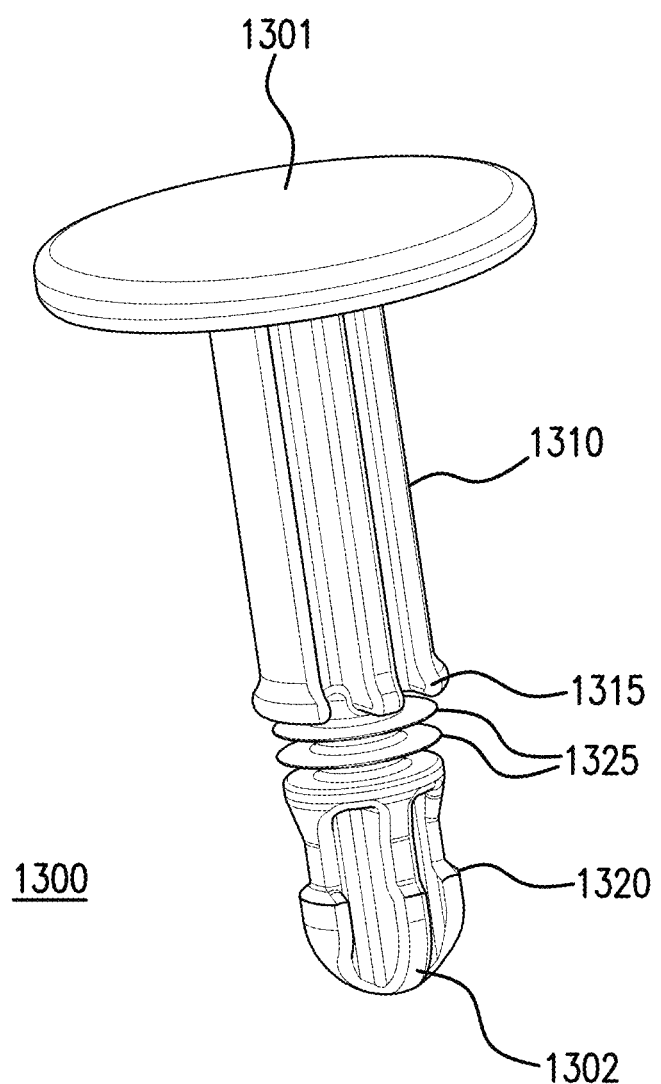
Figure 6C:
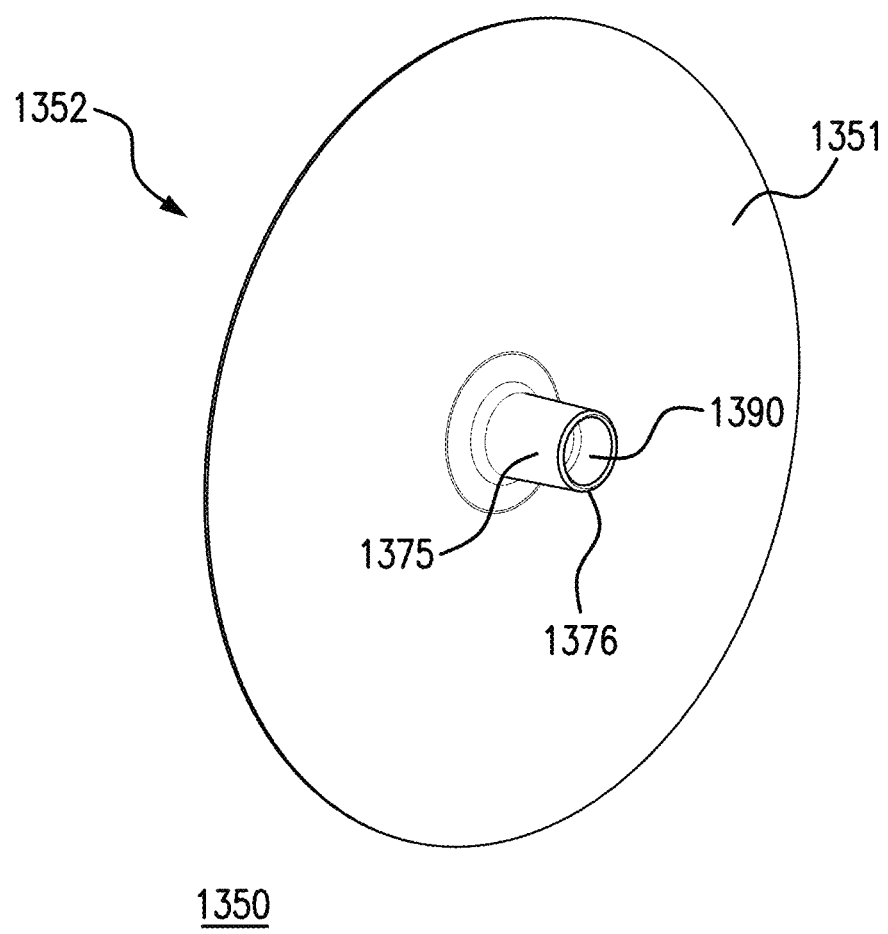

FIG. 6A is a perspective view of an impeller system according to an aspect of the invention, comprising the impeller assembly shown in FIG. 5A, wherein the impeller has a central opening, as well as a pin and seat fitment, the pin passing through the central opening into the seat fitment, for mounting the impeller system to a biocontainer comprising a closed container having an interior volume for containing fluid. FIG. 6B is a perspective view of the pin, FIG. 6C is a top perspective view of the seat fitment.

Figure 7A:
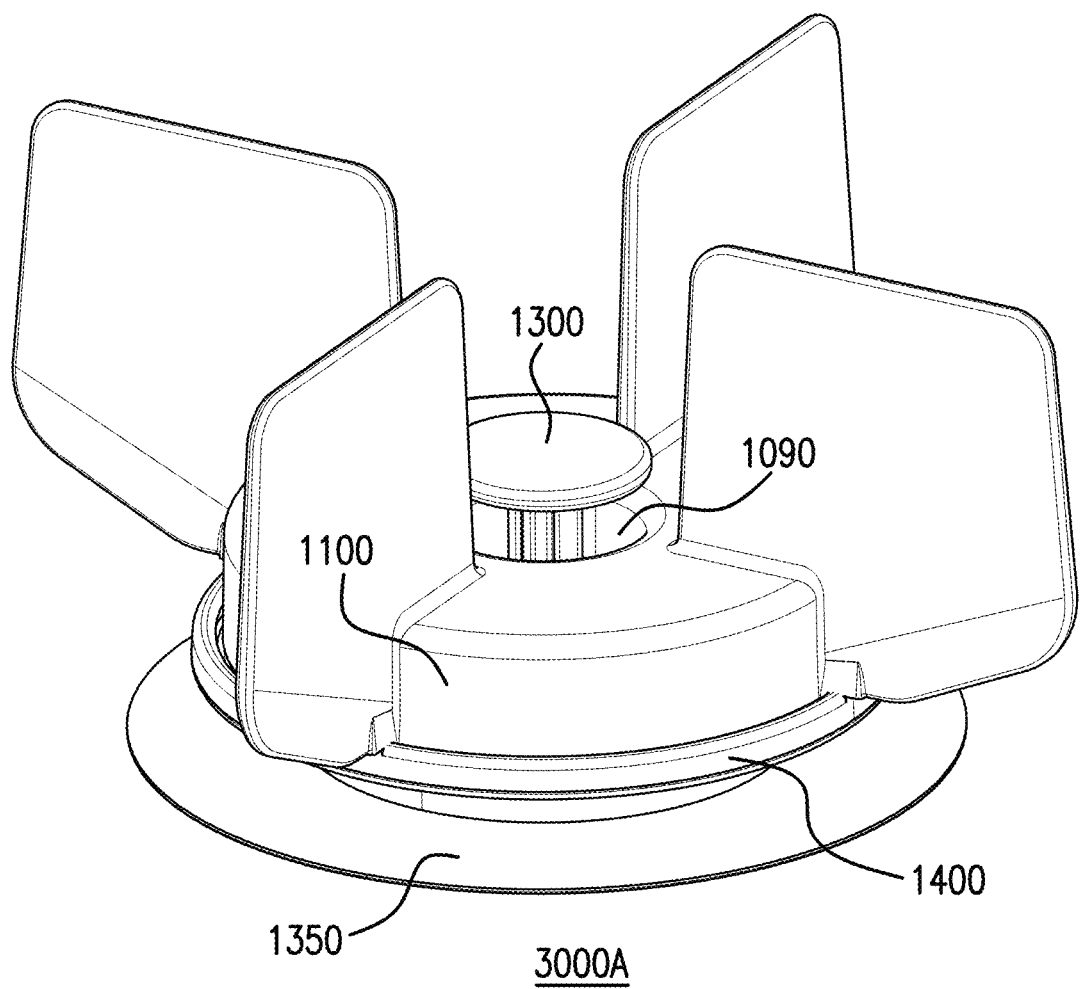
Figure 7B:
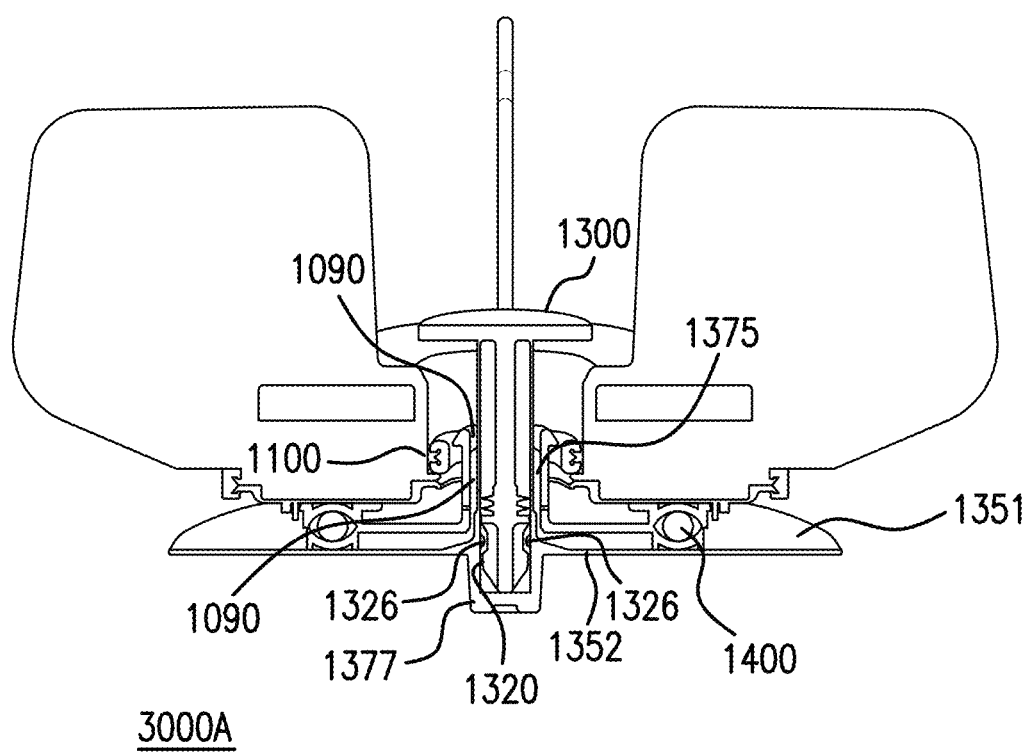

FIG. 7A is a perspective view of an impeller system according to another aspect of the invention, comprising an impeller assembly (with the guard removed for ease of viewing) including a base including bearings in a frame, as well as a pin and seat fitment, the pin passing through the central opening into the seat fitment, for mounting the impeller system to a biocontainer comprising a closed container having an interior volume for containing fluid. FIG. 7B is a cross-sectional view of the impeller system shown in FIG. 7A.

Figure 8:
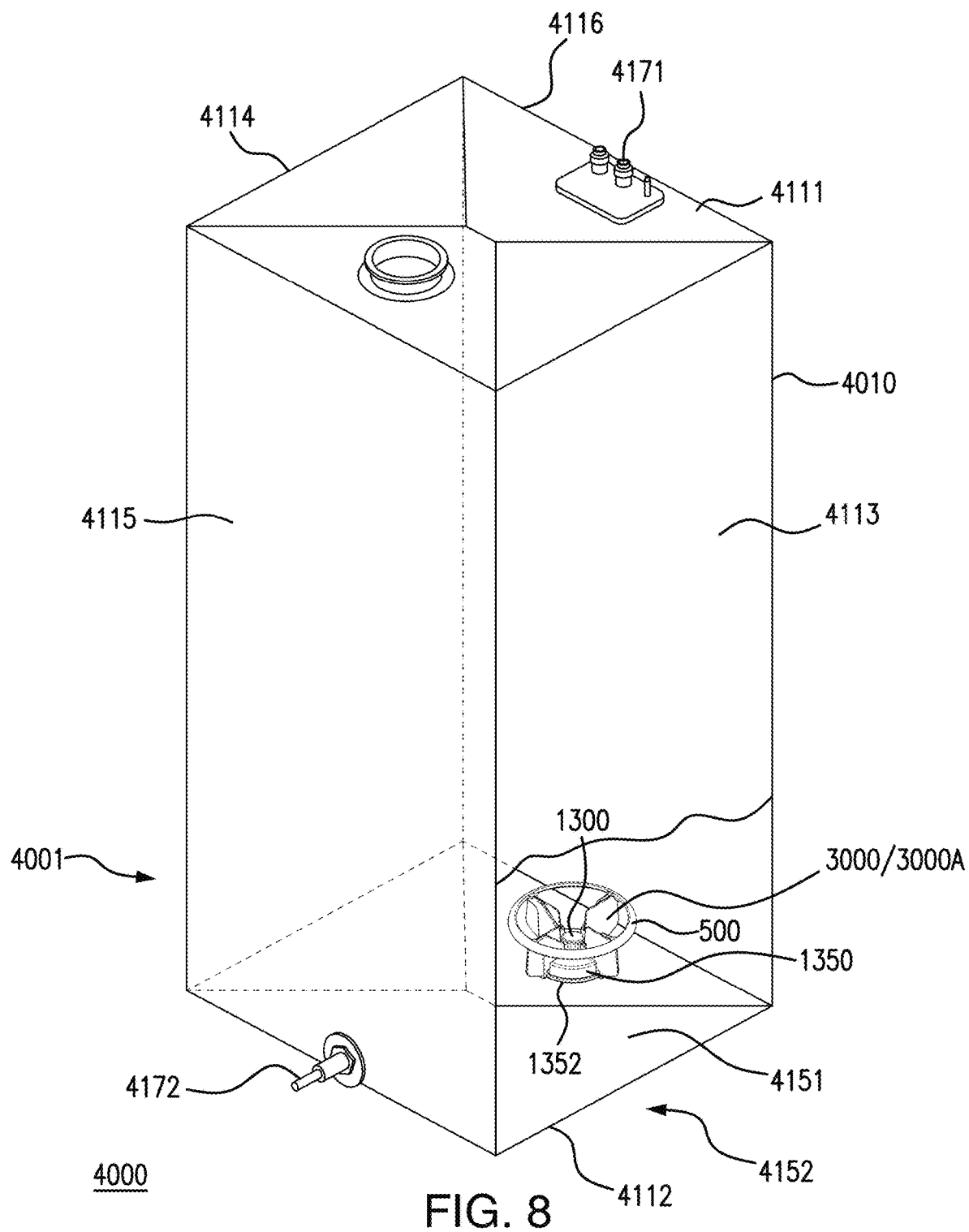

FIG. 8 is a side view of a biocontainer system according to an aspect of the invention, comprising a biocontainer comprising a closed container having an interior volume for containing fluid, also including the aspect of the impeller system shown in FIG. 6A, wherein the impeller is mounted to the biocontainer.

DETAILED DESCRIPTION OF THE INVENTION

An aspect of the invention provides a guard for an impeller having at least a first blade and a second blade, each of the first and second blades having front and rear blade faces, an upper edge, an outer edge, an upper outer corner where the upper edge contacts the outer edge, a lower edge, and an inner edge, the guard comprising: (A) an upper annular ring having an upper annular ring horizontal axis and a first internal diameter, the upper annular ring having an upper surface and a lower surface, wherein the lower surface includes at least a first blade receiving groove for receiving the upper outer corner of the first blade, the first blade receiving groove having first and second sides; and a second blade receiving groove for receiving the upper outer corner of the second blade, the second blade receiving groove having first and second sides; (B) a lower annular ring having a lower annular ring horizontal axis and a second internal diameter, wherein the second internal diameter is smaller than the first internal diameter; (C) at least a first brace member and a second brace member, each attached to the upper annular ring and the lower annular ring, each of the first brace member and second brace member being vertically arranged between the upper annular ring and the lower annular ring perpendicular to the upper annular ring horizontal axis and the lower annular ring horizontal axis, (1) the first brace member having a first brace member front wall, a first brace member rear wall, a first brace member outer side wall, and a first brace member inner side wall contacting the lower annular ring, the first brace member front wall or the first brace member rear wall being arranged to face a front or rear blade face of the first blade and forming the second side of the first blade receiving groove; (a) the first brace member having a vertical slot for receiving a portion of an inner edge of the first blade, and a catch for lockably receiving a portion of the lower edge of the first blade; (2) the second brace member having a second brace member front wall, a second brace member rear wall, a second brace member outer side wall and a second brace member inner side wall contacting the lower annular ring, the second brace member front wall or the second brace member rear wall being arranged to face a front or rear blade face of the second blade and forming the second side of the second blade receiving groove; (b) the second brace member having a vertical slot for receiving a portion of an inner edge of the second blade, and a catch for lockably receiving a portion of the lower edge of the second blade.

In some aspects of the guard, the lower surface of the upper annular ring includes a first protrusion spaced a distance from the front or rear blade face of the first blade and forming the first side of the first blade receiving groove, and a second protrusion spaced a distance from the front or rear blade face of the second blade and forming the first side of the second blade receiving groove.

Alternatively, or additionally, in some aspects, the first brace member inner side wall includes a first brace member extension forming a part of the vertical slot for receiving a portion of an inner edge of the first blade, and the second brace member inner side wall includes a second brace member extension forming a part of the vertical slot for receiving a portion of an inner edge of the second blade.

Alternatively, or additionally, in some aspects, the first brace member has a first brace member bottom end including the catch for lockably receiving the portion of the lower edge of the first blade, and the second brace member has a second brace member bottom end including the catch for lockably receiving the portion of the lower edge of the second blade.

In some aspects, the first brace member catch and the second brace member catch each comprise a hook.

In another aspect, an impeller assembly is provided, comprising: an impeller having at least a first blade and a second blade, each of the first and second blades having front and rear blade faces, an upper edge, an outer edge, an upper outer corner where the upper edge contacts the outer edge, a lower edge, and an inner edge; and a guard for the impeller, the guard comprising: (A) an upper annular ring having an upper annular ring horizontal axis and a first internal diameter, the upper annular ring having an upper surface and a lower surface, wherein the lower surface includes at least a first blade receiving groove for receiving the upper outer corner of the first blade, the first blade receiving groove having first and second sides; and a second blade receiving groove for receiving the upper outer corner of the second blade, the second blade receiving groove having first and second sides; (B) a lower annular ring having a lower annular ring horizontal axis and a second internal diameter, wherein the second internal diameter is smaller than the first internal diameter; (C) at least a first brace member and a second brace member, each attached to the upper annular ring and the lower annular ring, each of the first brace member and second brace member being vertically arranged between the upper annular ring and the lower annular ring perpendicular to the upper annular ring horizontal axis and the lower annular ring horizontal axis, (1) the first brace member having a first brace member front wall, a first brace member rear wall, a first brace member outer side wall, and a first brace member inner side wall contacting the lower annular ring, the first brace member front wall or the first brace member rear wall being arranged to face a front or rear blade face of the first blade and forming the second side of the first blade receiving groove; (a) the first brace member having a vertical slot for receiving a portion of an inner edge of the first blade, and a catch for lockably receiving a portion of the lower edge of the first blade; (2) the second brace member having a second brace member front wall, a second brace member rear wall, a second brace member outer side wall and a second brace member inner side wall contacting the lower annular ring, the second brace member front wall or the second brace member rear wall being arranged to face a front or rear blade face of the second blade and forming the second side of the second blade receiving groove; (b) the second brace member having a vertical slot for receiving a portion of an inner edge of the second blade, and a catch for lockably receiving a portion of the lower edge of the second blade, mounted to the impeller.

In yet another aspect, an impeller system is provided, comprising an aspect of the impeller assembly comprising: an impeller having at least a first blade and a second blade, each of the first and second blades having front and rear blade faces, an upper edge, an outer edge, an upper outer corner where the upper edge contacts the outer edge, a lower edge, and an inner edge; and a guard for the impeller, the guard comprising: (A) an upper annular ring having an upper annular ring horizontal axis and a first internal diameter, the upper annular ring having an upper surface and a lower surface, wherein the lower surface includes at least a first blade receiving groove for receiving the upper outer corner of the first blade, the first blade receiving groove having first and second sides; and a second blade receiving groove for receiving the upper outer corner of the second blade, the second blade receiving groove having first and second sides; (B) a lower annular ring having a lower annular ring horizontal axis and a second internal diameter, wherein the second internal diameter is smaller than the first internal diameter; (C) at least a first brace member and a second brace member, each attached to the upper annular ring and the lower annular ring, each of the first brace member and second brace member being vertically arranged between the upper annular ring and the lower annular ring perpendicular to the upper annular ring horizontal axis and the lower annular ring horizontal axis, (1) the first brace member having a first brace member front wall, a first brace member rear wall, a first brace member outer side wall, and a first brace member inner side wall contacting the lower annular ring, the first brace member front wall or the first brace member rear wall being arranged to face a front or rear blade face of the first blade and forming the second side of the first blade receiving groove; (a) the first brace member having a vertical slot for receiving a portion of an inner edge of the first blade, and a catch for lockably receiving a portion of the lower edge of the first blade; (2) the second brace member having a second brace member front wall, a second brace member rear wall, a second brace member outer side wall and a second brace member inner side wall contacting the lower annular ring, the second brace member front wall or the second brace member rear wall being arranged to face a front or rear blade face of the second blade and forming the second side of the second blade receiving groove; (b) the second brace member having a vertical slot for receiving a portion of an inner edge of the second blade, and a catch for lockably receiving a portion of the lower edge of the second blade, mounted to the impeller; a pin, and a seat fitment.

In another aspect, a biocontainer system is provided, comprising: (a) a biocontainer comprising a closed container having an interior volume suitable for containing fluid, the container comprising a bottom wall, a top wall, at least one side wall, the side wall(s) being joined to the top wall and the bottom wall; and at least an inlet port, and a drain port, wherein the biocontainer further comprises: (b) an aspect of the impeller system comprising an aspect of the impeller assembly comprising: an impeller having at least a first blade and a second blade, each of the first and second blades having front and rear blade faces, an upper edge, an outer edge, an upper outer corner where the upper edge contacts the outer edge, a lower edge, and an inner edge; and a guard for the impeller, the guard comprising: (A) an upper annular ring having an upper annular ring horizontal axis and a first internal diameter, the upper annular ring having an upper surface and a lower surface, wherein the lower surface includes at least a first blade receiving groove for receiving the upper outer corner of the first blade, the first blade receiving groove having first and second sides; and a second blade receiving groove for receiving the upper outer corner of the second blade, the second blade receiving groove having first and second sides; (B) a lower annular ring having a lower annular ring horizontal axis and a second internal diameter, wherein the second internal diameter is smaller than the first internal diameter; (C) at least a first brace member and a second brace member, each attached to the upper annular ring and the lower annular ring, each of the first brace member and second brace member being vertically arranged between the upper annular ring and the lower annular ring perpendicular to the upper annular ring horizontal axis and the lower annular ring horizontal axis, (1) the first brace member having a first brace member front wall, a first brace member rear wall, a first brace member outer side wall, and a first brace member inner side wall contacting the lower annular ring, the first brace member front wall or the first brace member rear wall being arranged to face a front or rear blade face of the first blade and forming the second side of the first blade receiving groove; (a) the first brace member having a vertical slot for receiving a portion of an inner edge of the first blade, and a catch for lockably receiving a portion of the lower edge of the first blade; (2) the second brace member having a second brace member front wall, a second brace member rear wall, a second brace member outer side wall and a second brace member inner side wall contacting the lower annular ring, the second brace member front wall or the second brace member rear wall being arranged to face a front or rear blade face of the second blade and forming the second side of the second blade receiving groove; (b) the second brace member having a vertical slot for receiving a portion of an inner edge of the second blade, and a catch for lockably receiving a portion of the lower edge of the second blade, mounted to the impeller; a pin, and a seat fitment; wherein the impeller is mounted to an inner surface of the bottom wall of the biocontainer.

In yet another aspect, a method for mounting as aspect of the guard to an impeller is provided, the method comprising: positioning the inner edges of the blades of the impeller in the vertical slots of the respective brace members; positioning the upper outer corners of the blades of the impeller in the respective blade receiving grooves; and positioning the lower edges of the blades of the impeller in the catches of the respective brace members.

Aspects of the invention are especially suitable for use in closed and/or sterile systems.

Each of the components of the invention will now be described in more detail below, wherein like components have like reference numbers.

Figure 4A:
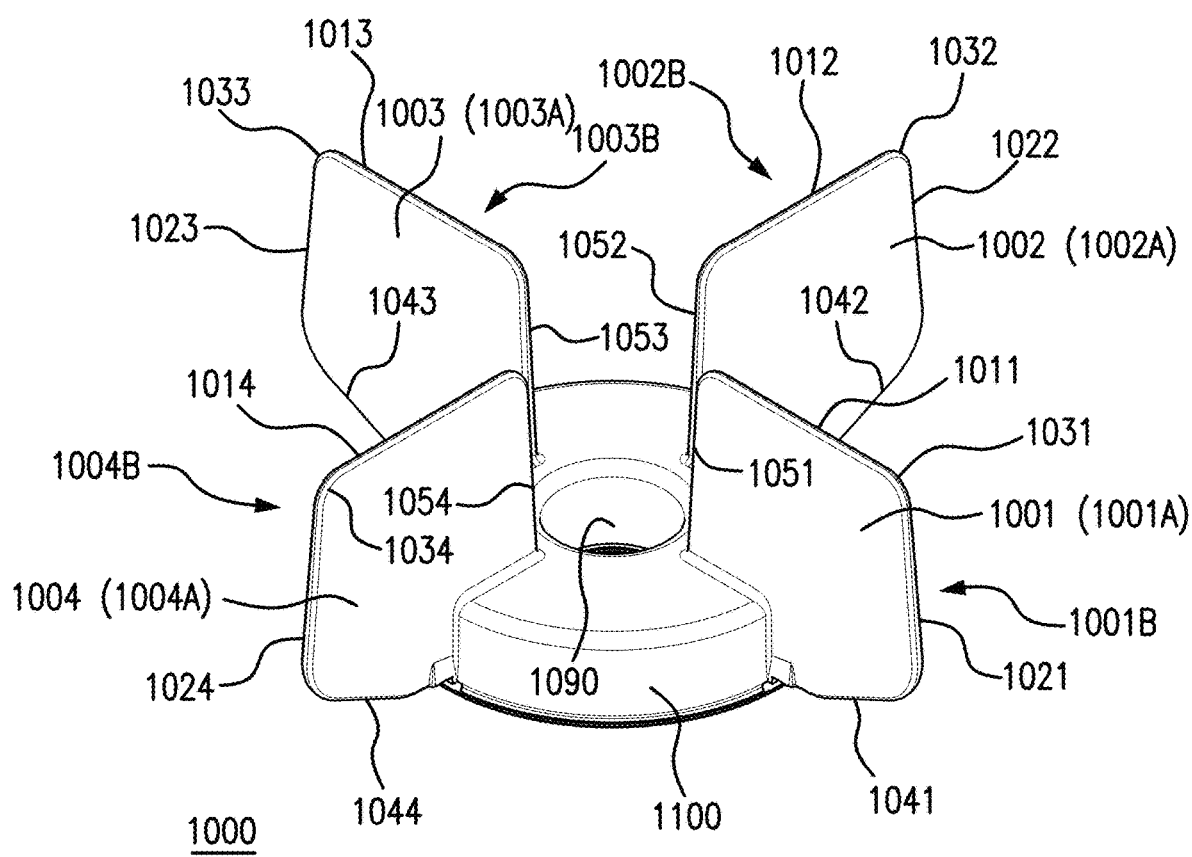
FIGS. 4A and 4B are, respectively, a top perspective view, and a top view, of an impeller suitable for use with a guard according to an aspect of the invention.
Figure 4B:
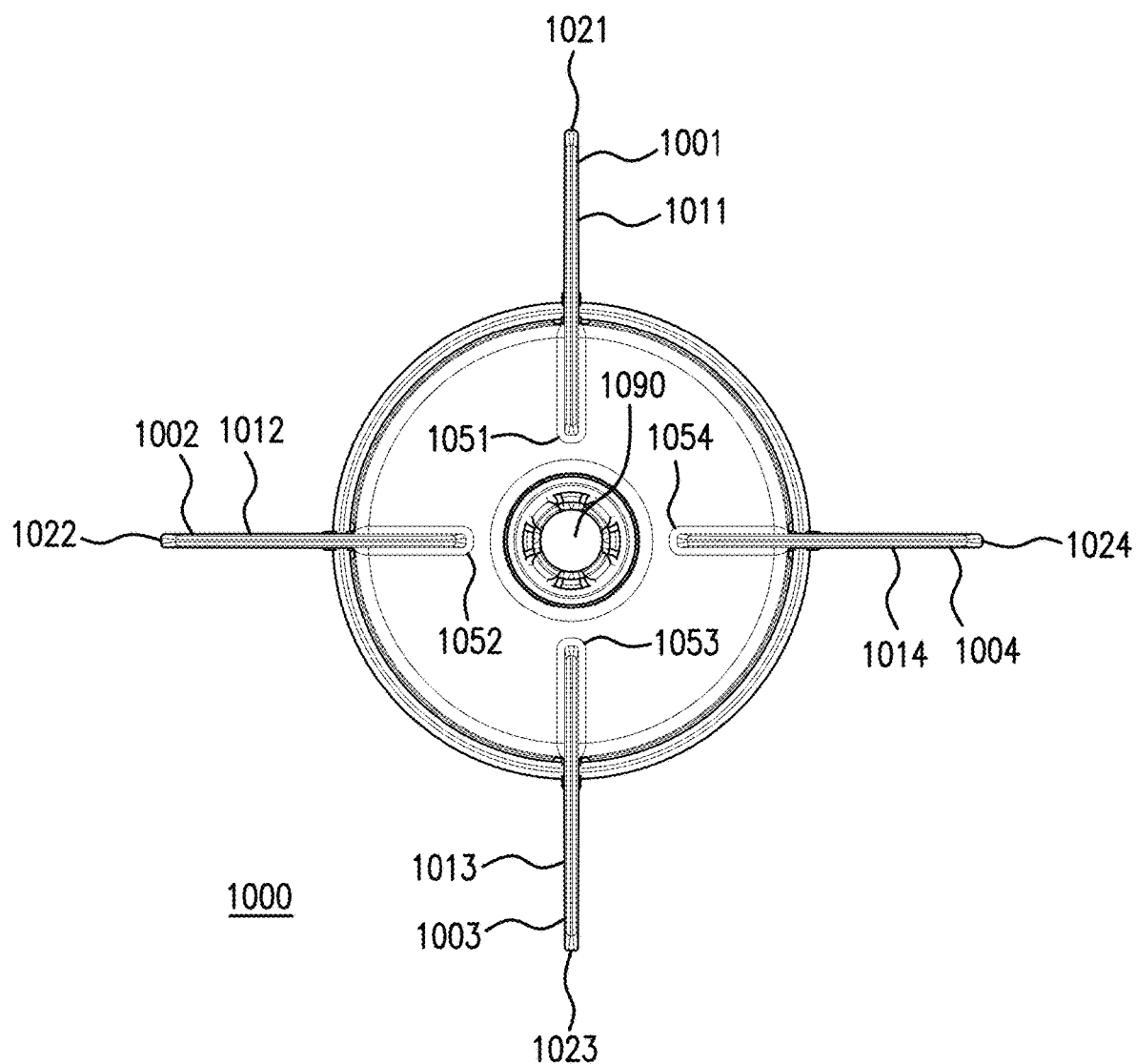

While suitable impellers can have variety of configurations and any number of blades, FIGS. 4A and 4B show an illustrative impeller 1000 having, attached to a hub 1100 having a central opening 1090, four blades: first blade 1001, second blade 1002, third blade 1003, and fourth blade 1004, the respective blades having front and rear blade faces 1001A, 1001B; 1002A, 1002B; 1003A, 1003C; and 1004A, 1004B. Each blade has, respectively, an upper edge 1011, 1012, 1013, 1014, an outer edge 1021, 1022, 1023, 1024, an upper outer corner 1031, 1032, 1033, 1034, where the upper edge contacts the outer edge, a lower edge 1041, 1042, 1043, 1044, and an inner edge 1051, 1052, 1053, 1054.

In preferred aspects, the impeller is a magnetic impeller, in some aspects, a levitating magnetic impeller. If desired, at certain times, a removable metal plate can be placed in contact with the bottom surface of the magnetic impeller, to provide a guard minimizing, if not eliminating, the possible effect of the magnetic field on nearby devices or components.

Using the aspect shown in FIGS. 1A, 1B, 2A, 2B, and 3 for reference, a guard 500 with blade receivers 300 for an impeller having at least a first blade and a second blade, each of the first and second blades having front and rear blade faces, an upper edge, an outer edge, an upper outer corner where the upper edge contacts the outer edge, a lower edge, and an inner edge (the impeller as shown in FIGS. 4A and 4B), comprises an upper annular ring 100 having an upper annular ring horizontal axis HA1 (FIG. 3) and a first internal diameter 175, the upper annular ring having an upper surface

101 and a lower surface 102, wherein the lower surface includes at least a first blade receiving groove 371 for receiving the upper outer corner of the first blade (see, FIG. 5A), the first blade receiving groove having first and second sides 371A, 371B (see, FIG. 2B); and a second blade receiving groove 372 for receiving the upper outer corner of the second blade, the second blade receiving groove having first and second sides 372A, 372B. In the illustrated aspects, the impeller includes four blades, and the guard includes third and fourth blade receiving grooves 373, 374, with respective first and second sides 373A, 373B, 374A, 374B, for receiving respective upper outer corners of the third and fourth blades.

In the illustrated aspects, a lower annular ring 200 has a lower annular ring horizontal axis HA2 (FIG. 3), and a second internal diameter 275, wherein the second internal diameter 275 is smaller than the first internal diameter 175; at least a first brace member 301 and a second brace member 302, each attached to the upper annular ring and the lower annular ring, each of the first brace member and second brace member being vertically arranged VA between the upper annular ring and the lower annular ring perpendicular to the upper annular ring horizontal axis and the lower annular ring horizontal axis, the first brace member 301 having a first brace member front wall 301A, a first brace member rear wall 301B, a first brace member outer side wall 301C, and a first brace member inner side wall 301D contacting the lower annular ring, the first brace member front wall or the first brace member rear wall being arranged to face a front or rear blade face of the first blade and forming the second side 371B of the first blade receiving groove 371; (a) the first brace member having a vertical slot 361 for receiving a portion of an inner edge of the first blade, and a catch 381 for lockably receiving a portion of the lower edge of the first blade (see, FIGS. 5A and 5B); the second brace member 302 having a second brace member front wall 302A, a second brace member rear wall 302B, a second brace member outer side wall 302C and a second brace member inner side wall 302D contacting the lower annular ring, the second brace member front wall or the second brace member rear wall being arranged to face a front or rear blade face of the second blade and forming the second side 372B of the second blade receiving groove 372; (b) the second brace member having a vertical slot 362 for receiving a portion of an inner edge of the second blade, and a catch 382 for lockably receiving a portion of the lower edge of the second blade. In the illustrated aspects, the impeller includes four blades, and the guard includes third and fourth brace members 303, 304, with respective front, rear, outer and inner walls, 303A, 303B, 303C, 303D, 304A, 304B, 304C, 304D, vertical slots, 363, 364, and catches 383, 384.

If desired (see, FIG. 2B), the lower surface 102 of the upper annular ring can include a first protrusion 351 (shown as doubled protrusions if increased robustness is desired) spaced a distance from the front or rear blade face of the first blade and forming the first side 371A of the first blade receiving groove 371, and a second protrusion 352 (shown as doubled protrusions if increased robustness is desired) spaced a distance from the front or rear blade face of the second blade and forming the first side 372A of the second blade receiving groove 372. The illustrated aspects also show third and fourth protrusions 353, 354 (each shown as doubled protrusions if increased robustness is desired), forming first sides 353A, 354A, of the respective third and fourth blade receiving grooves 373, 374. If desired, the upper corners of the protrusions leading to the first side of the blade receiving grooves can be angled downwardly (see, FIG. 1B showing 351A, 352A, 353A, and 354A), for ease of guiding the upper outer corners of the blades into the blade receiving grooves.

Preferably, the first brace member inner side wall 301D includes a first brace member extension 311 forming a part of the vertical slot 361 for receiving a portion of an inner edge of the first blade, and the second brace member inner side wall 302D includes a second brace member extension 312 forming a part of the vertical slot 362 for receiving a portion of an inner edge of the second blade. The illustrated aspect also show third and fourth brace member inner side walls including extensions 313, 314, forming vertical slots 363, 364. Illustratively, the brace member inner side walls can include "J-," "L-," or "C-shaped" arms forming one inner side of the slots, wherein the brace member front or rear wall forms the opposing inner side of the slot (see, for example, arm 311A and front wall 301A, as well as arms 312A and 314A, in FIG. 1A)

In the illustrated aspect, the first brace member 301 has a first brace member bottom end 331 including the catch 381 for lockably receiving the portion of the lower edge of the first blade (see, FIG. 5A), and the second brace member 302 has a second brace member bottom end 332 including the catch 382 for lockably receiving the portion of the lower edge of the second blade. The illustrated aspect also show third and fourth brace member bottom ends 333, 334 including the catches 383, 384.

Preferably, for ease of lockably receiving portions of the lower edges of the blades, brace member catches 381, 382 each respective comprise a hook (curved or bent back at an angle) 391, 392, wherein the figures also show catches 383, 384, respectively comprising hooks 393, 394.

Figure 1A:
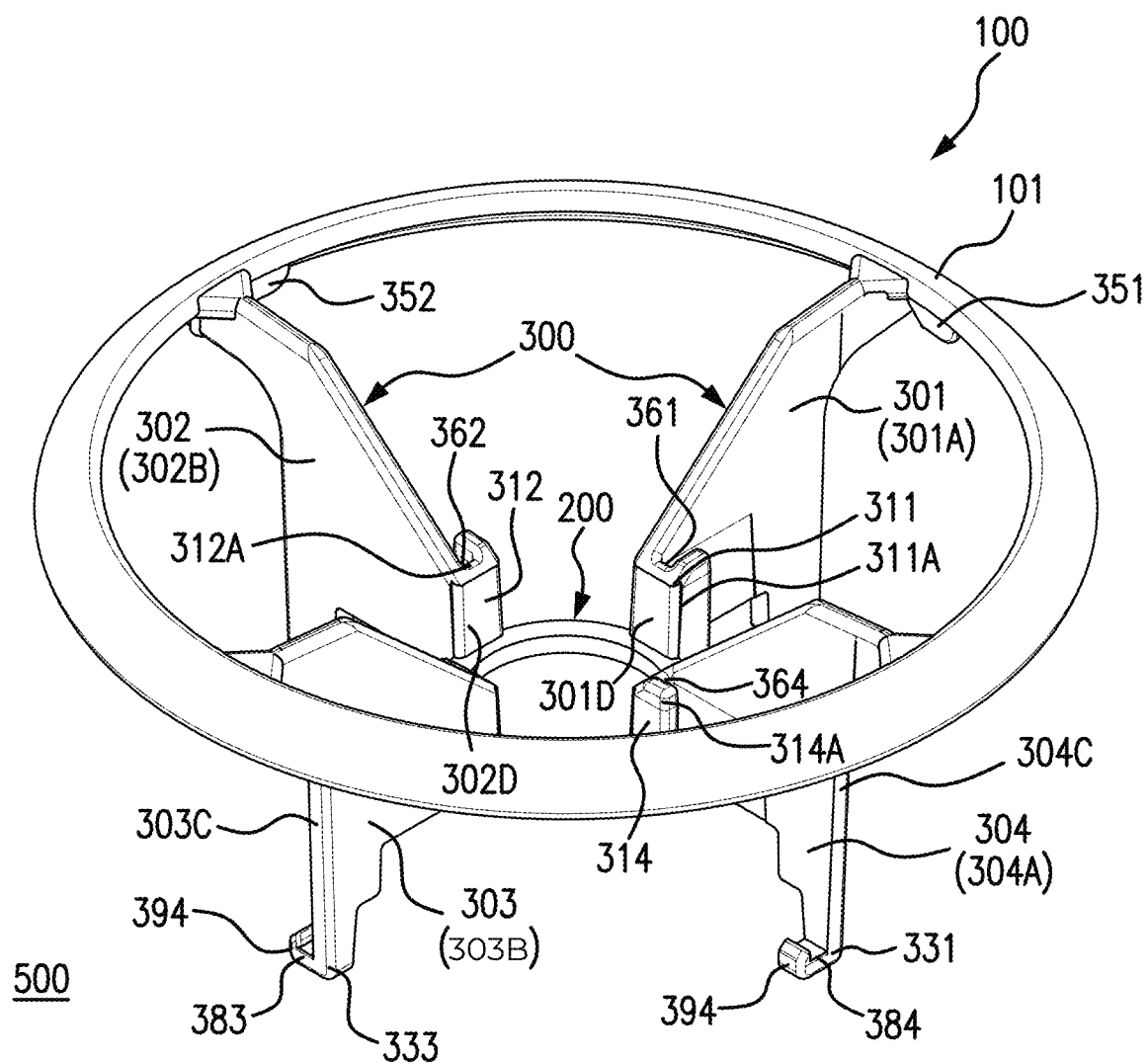
FIGS. 1A and 1B are, respectively, top and bottom perspective views of a guard for an impeller according to an aspect of the invention.
Figure 1B:
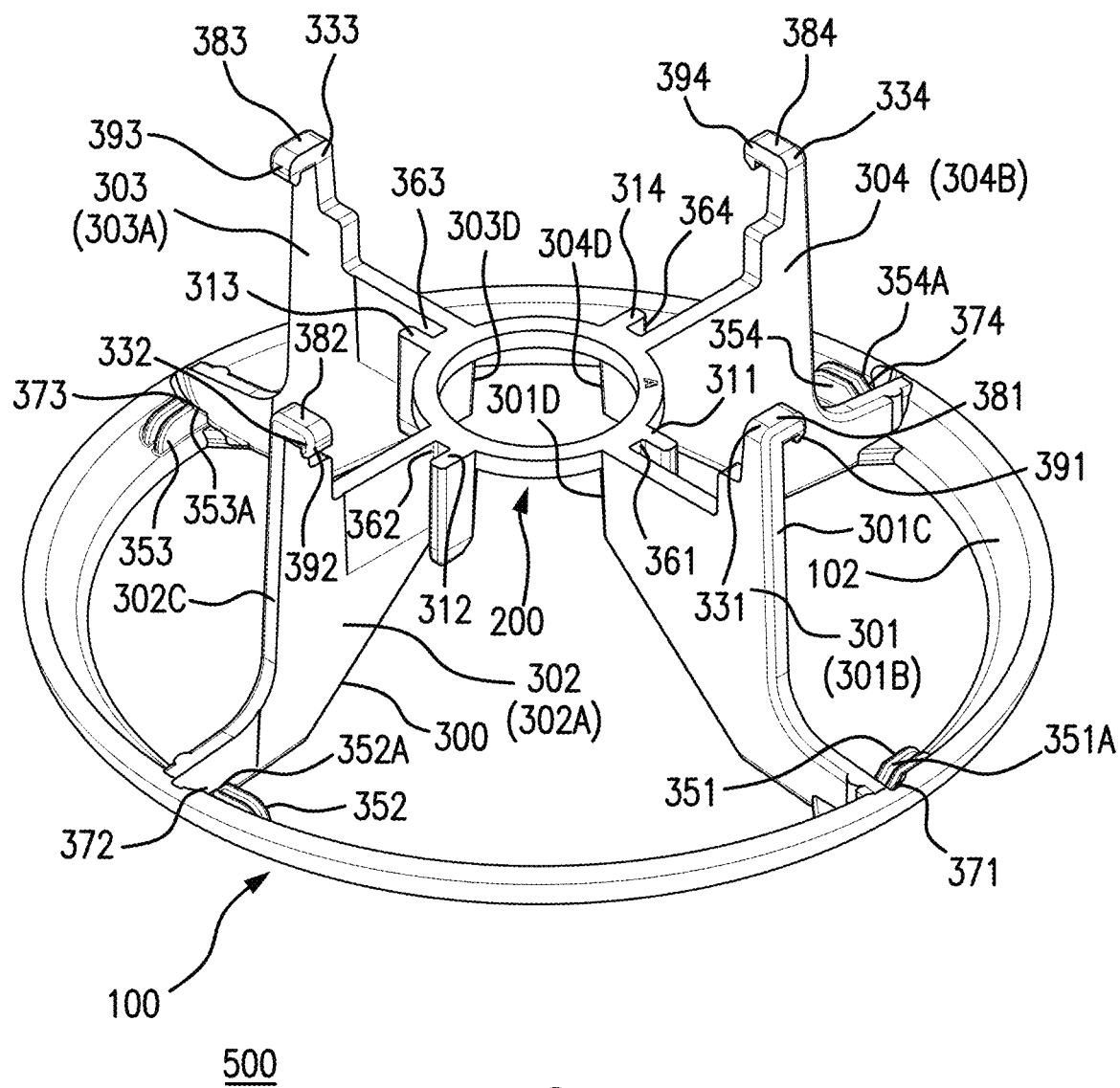
Figure 2A:
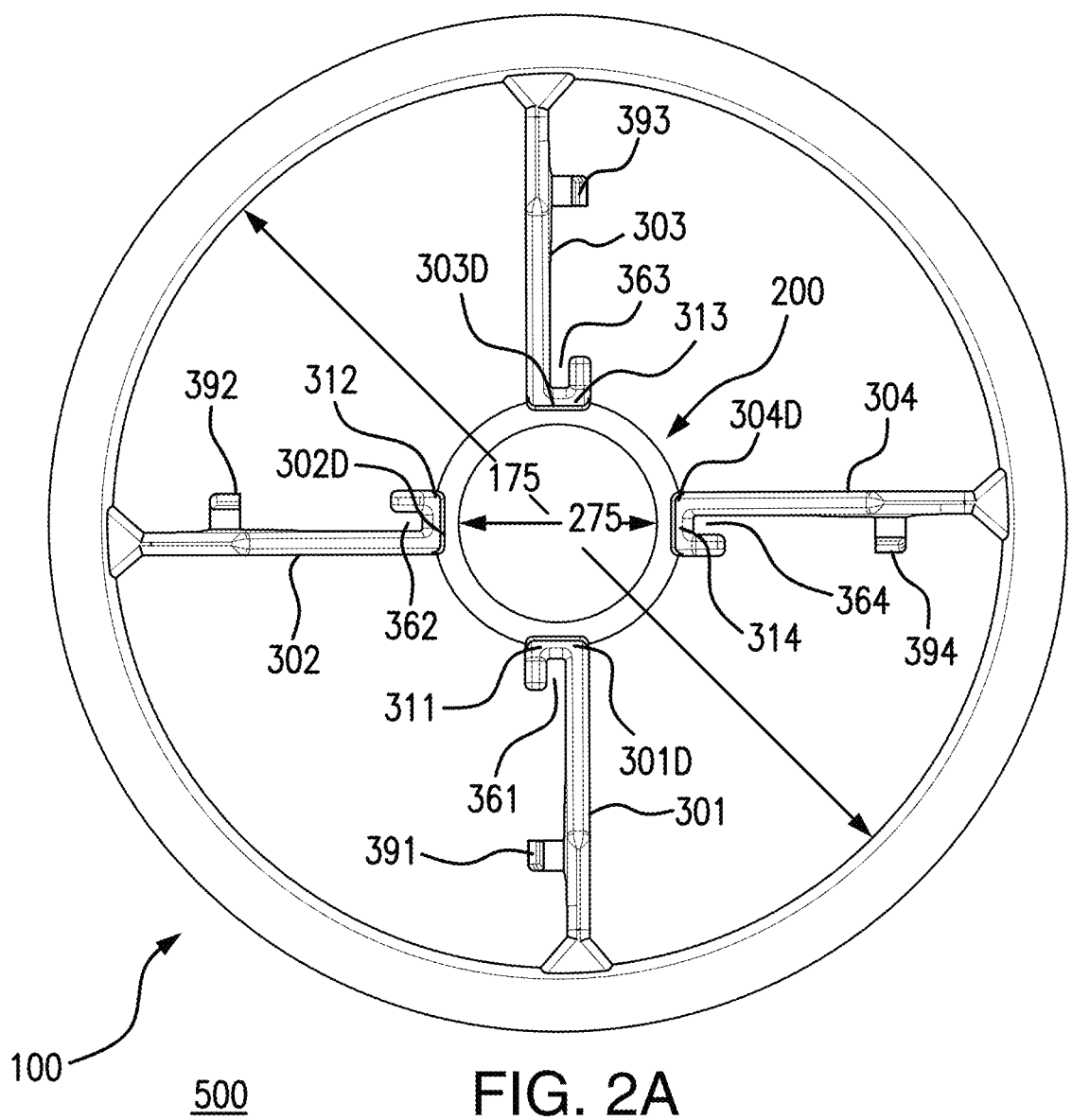
FIGS. 2A and 2B are, respectively, top and bottom views of the aspect of the guard shown in FIG. 1A.
Figure 2B:
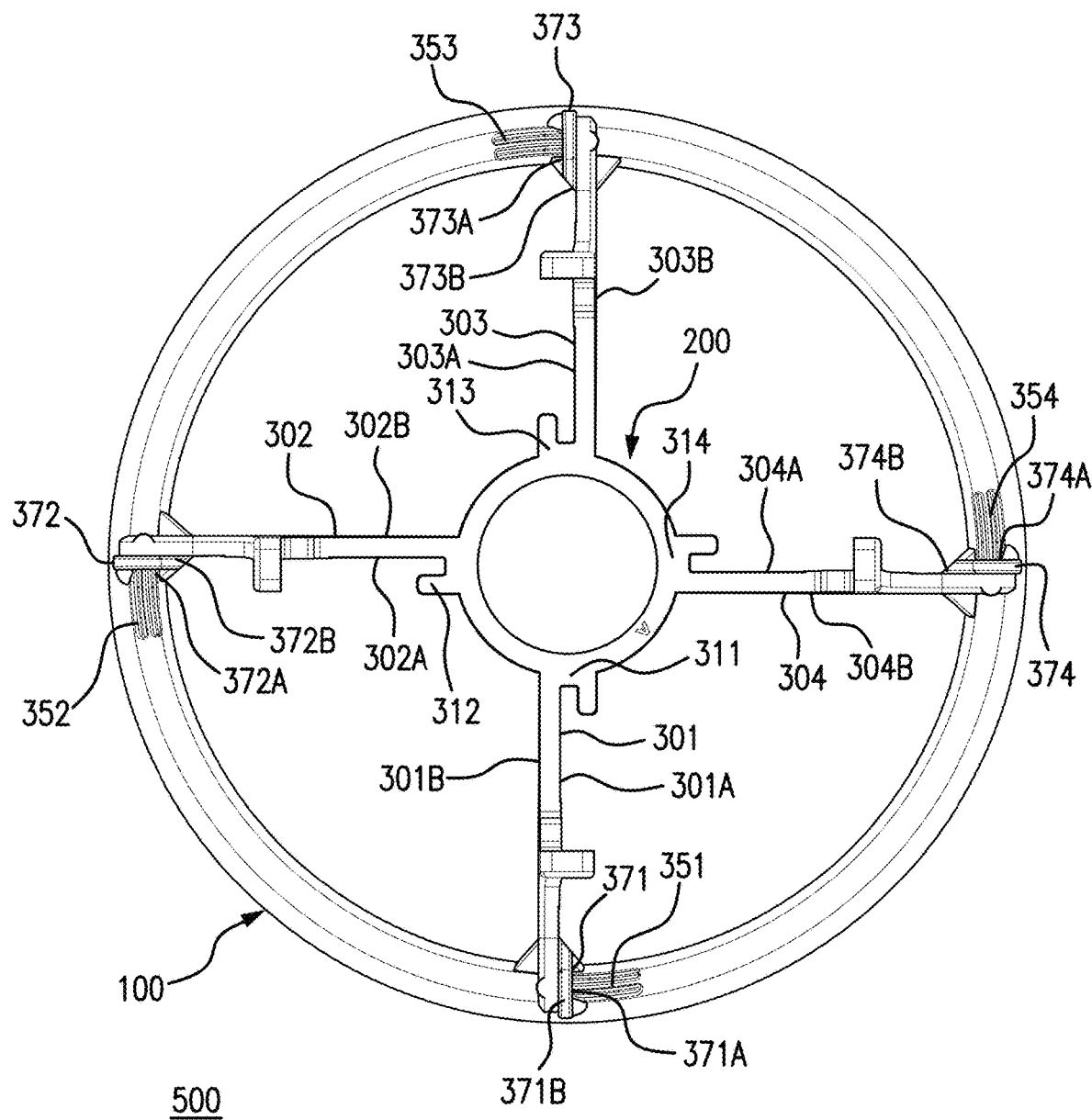
Figure 3:
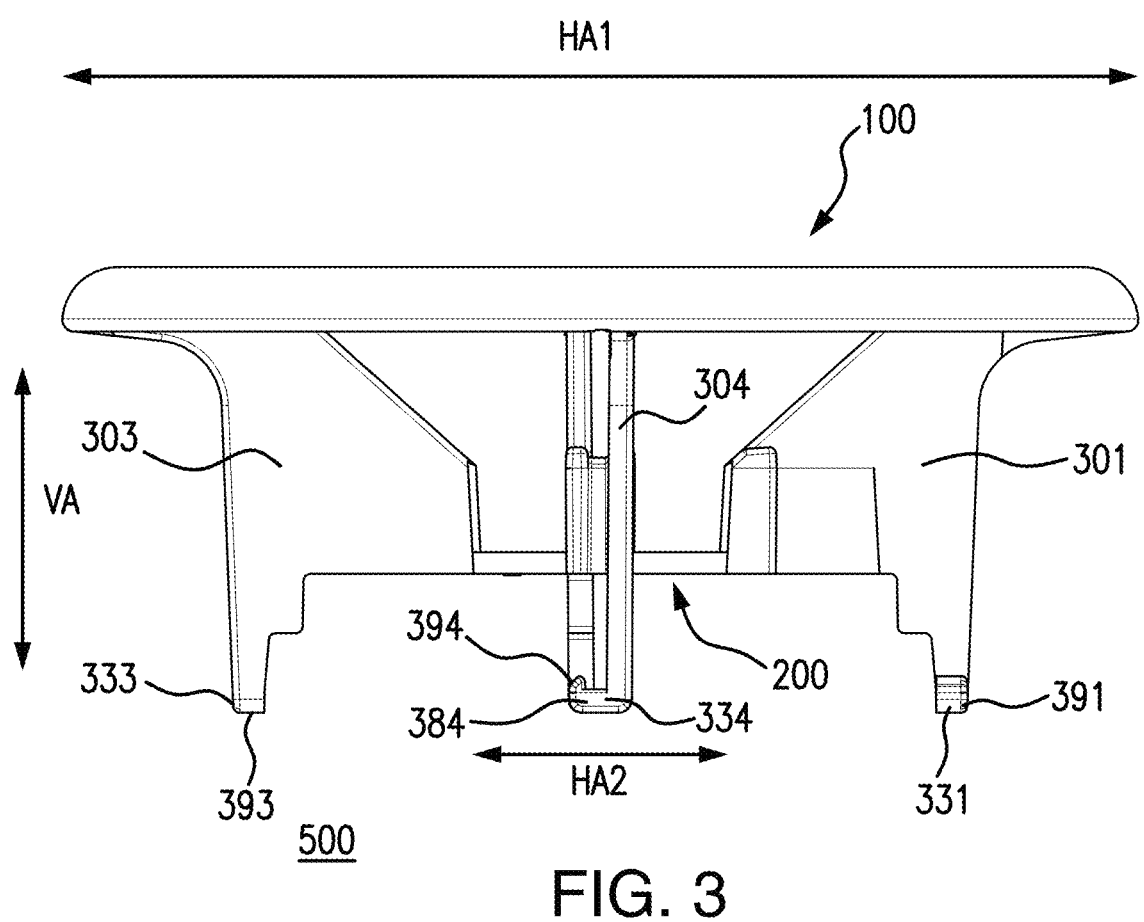
FIG. 3 is a side view of the aspect of the guard shown in FIG. 1A.
Figure 5B:
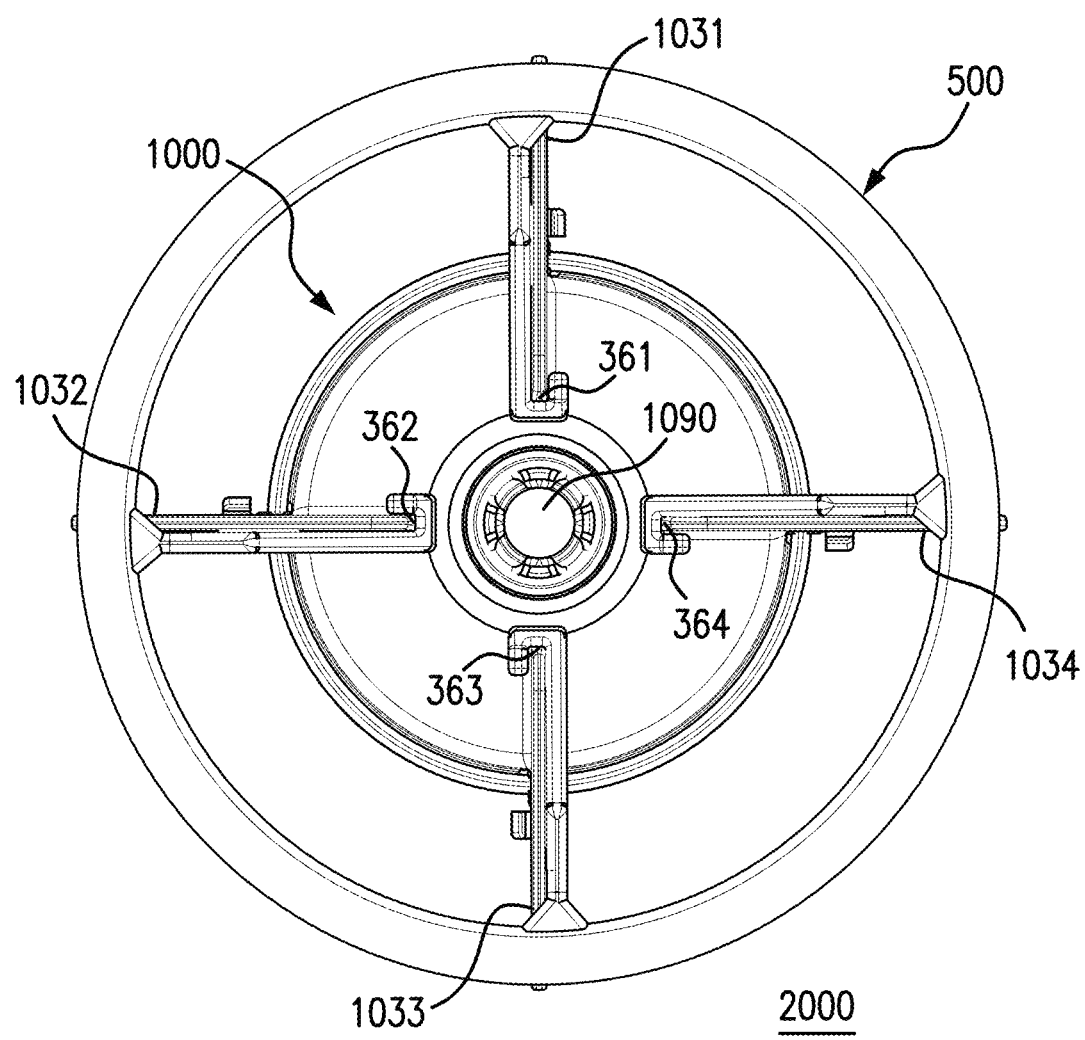

FIGS. 5A and 5B show an impeller assembly 2000 according to an aspect of the invention, wherein the aspect of the guard 500 shown in FIG. 1A is engaged with the aspect of the impeller 1000 shown in FIG. 4A, wherein portions of the blades are received in the components of the guard as discussed above. Thus, the inner edges of the blades are positioned in the vertical slots of the guard, the upper outer corners of the blades are positioned in the blade receiving grooves, optionally after contacting the protrusions wherein contacting the angled portions of the protrusions helps guide the upper outer corners into the blade receiving grooves, and the portions of the lower edges of the blades are lockably received in the catches. In this context, "lockably received" indicates that removing the lower edges of the blades from the catches is difficult.

FIG. 6A shows a perspective view an impeller assembly 3000 according to an aspect of the invention, comprising the aspect of the impeller assembly shown in FIGS. 5A and 5B wherein the assembly further comprising a pin 1300 and a seat fitment 1350, for mounting on a biocontainer (biocontainer 4001 shown in FIG. 8). As shown in FIG. 6B, the illustrated pin 1300 has a head 1301, a tip 1302, a shaft 1310 connected to the head at one end and the tip at the other end, wherein the shaft also includes ribs 1315 and the tip includes a ridge 1320, the pin having chamfers 1325 between the shaft and the tip. As shown in FIG. 6C, the seat fitment 1350 has a first (upper) surface 1351 and a second (lower) surface 1352. As will be discussed in more detail below, the lower surface 1352 will be secured to (e.g., welded) to the inner surface of the biocontainer.

The illustrated fitment 1350 has a hollow extension 1375 with a central opening 1390 at a first (upper) end 1376 of the extension for receiving the pin 1300, wherein the fitment 1350 also includes an internal fitment chamfer 1326 (shown in FIG. 7B). FIG. 6C shows the extension extending upwardly from the first surface 1351, the extension also extends downwardly from the lower surface 1352 and is closed and the second (lower) end (see, FIG. 7B showing another aspect of an impeller assembly 3000A wherein the extension includes a closed lower end 1377). Once the pin 1300 is fully inserted through the impeller opening 1090 and the fitment opening 1390, the ridge 1320 provides a friction fit against the lower portion of the fitment chamfer 1326, and the pin chamfers 1325 also provide friction, preventing the pin from disengaging from the fitment.

FIGS. 7A (perspective view) and 7B (sectional view) show another impeller assembly 3000A according to an aspect of the invention, generally similar to the aspect shown in FIG. 6A. However, the aspect shown in FIGS. 7A and 7B includes a bearing assembly 1400 arranged between the hub of the impeller and the first surface 1351 of the seat fitment 1350. As with the impeller assembly 3000, the illustrated aspect of impeller assembly 3000A includes a pin 1300 fully inserted through the impeller opening 1090 and the fitment opening 1390, the ridge 1320 provides a friction fit against the lower portion of the fitment chamfer 1326, and the pin chamfers 1325 also provide friction, preventing the pin from disengaging from the fitment.

Aspects of the invention are suitable for use with a wide variety of biocontainers and biocontainer systems, preferably, single-use biocontainers and biocontainer systems, and/or for maintaining closed, sterile systems. Biocontainers can have, for example, any suitable shape and interior volume, and any number of ports and/or fittings and/or fluid conduits such as tubing. Biocontainers have at least two ports, i.e., an inlet port and a drain port, and may have one or more additional ports, e.g., one or more of any of the following: for sampling, venting, monitoring (e.g., any one or more of the following: oxygen, temperature, pH), and additives. Biocontainers comprises a bottom wall, a top wall, and at least one side wall, the side wall(s) being joined to the top wall and the bottom wall.

FIG. 8 shows an illustrative biocontainer system 4000 according to an aspect of the invention, comprising a biocontainer 4001 comprising a closed container having an interior volume for containing fluid, wherein an the aspect of the impeller system (e.g., as shown in FIG. 6A or 7A) is mounted on the biocontainer 4001. The illustrated biocontainer 4001 comprises a flexible biocontainer bag 4010, the bag comprising an inlet port 4171, an outlet port 4172, a top wall 4111, a bottom wall 4112 having an inner surface 4151 and an outer surface 4152, and opposing side walls 4113, 4114, 4115, 4116, providing an interior volume therein, wherein the aspect of the impeller system such that the lower surface 1352 of the seat fitment 1350 is secured to (e.g., welded) to the inner surface 1451 of the biocontainer. While not shown in FIG. 8, the closed lower end 1377 of the seat fitment extension passes through the outer surface 4152 of the biocontainer for cooperation with a drive system including a motor for rotating the impeller.

A number of materials and processes are suitable for producing guards according to aspects of the invention. Suitable materials include for example, thermoplastic resins such as polypropylene, and polyethylene (e.g., high density polyethylene). A suitable process includes, for example, injection molding.

A variety of impellers are suitable for use in aspects of the invention, and are commercially available. Suitable impellers include magnetic and levitating impellers, for example, available under the names LEVMIXER® mixer and ALLEGRO™ Magnetic Mixer (Pall Corporation, East Hills, NY).

A variety of biocontainers and biocontainer systems impellers are suitable for use in aspects of the invention (i.e., impeller systems according to aspects of the system can be mounted on the biocontainers), and are commercially available.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred aspects of this invention are described herein, including the best mode known to the inventors for carrying out the invention. Variations of those preferred aspects may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A guard for an impeller having at least a first blade and a second blade, each of the first and second blades having front and rear blade faces, an upper edge, an outer edge, an upper outer corner where the upper edge contacts the outer edge, a lower edge, and an inner edge, the guard comprising:
    (A) an upper annular ring having an upper annular ring horizontal axis and a first internal diameter, the upper annular ring having an upper surface and a lower surface, wherein the upper surface further comprises a peripheral edge having a rounded surface and wherein the lower surface includes at least a first blade receiving groove for receiving the upper outer corner of the first blade, the first blade receiving groove having first and second sides; and a second blade receiving groove for receiving the upper outer corner of the second blade, the second blade receiving groove having first and second sides;

(B) a lower annular ring having a lower annular ring horizontal axis and a second internal diameter, wherein the second internal diameter is smaller than the first internal diameter;

(C) at least a first brace member and a second brace member, each attached to the upper annular ring and the lower annular ring, each of the first brace member and second brace member being vertically arranged between the upper annular ring and the lower annular ring perpendicular to the upper annular ring horizontal axis and the lower annular ring horizontal axis, (1) the first brace member having a first brace member front wall, a first brace member rear wall, a first brace member outer side wall, and a first brace member inner side wall contacting the lower annular ring, the first brace member front wall or the first brace member rear wall being arranged to face a front or rear blade face of the first blade and forming the second side of the first blade receiving groove;

(a) the first brace member having a vertical slot for receiving a portion of an inner edge of the first blade, and a catch for lockably receiving a portion of the lower edge of the first blade;

(2) the second brace member having a second brace member front wall, a second brace member rear wall, a second brace member outer side wall and a second brace member inner side wall contacting the lower annular ring, the second brace member front wall or the second brace member rear wall being arranged to face a front or rear blade face of the second blade and forming the second side of the second blade receiving groove;

(b) the second brace member having a vertical slot for receiving a portion of an inner edge of the second blade, and a catch for lockably receiving a portion of the lower edge of the second blade.

2. The guard of claim 1, wherein the first brace member catch and the second brace member catch each comprise a hook.

3. The guard of claim 1, wherein the first brace member has a first brace member bottom end including the catch for lockably receiving the portion of the lower edge of the first blade, and the second brace member has a second brace member bottom end including the catch for lockably receiving the portion of the lower edge of the second blade.

4. The guard of claim 3, wherein the first brace member catch and the second brace member catch each comprise a hook.

5. The guard of claim 1, wherein the first brace member inner side wall includes a first brace member extension forming a part of the vertical slot for receiving a portion of an inner edge of the first blade, and the second brace member inner side wall includes a second brace member extension forming a part of the vertical slot for receiving a portion of an inner edge of the second blade.

6. The guard of claim 5, wherein the first brace member has a first brace member bottom end including the catch for lockably receiving the portion of the lower edge of the first blade, and the second brace member has a second brace member bottom end including the catch for lockably receiving the portion of the lower edge of the second blade.

7. The guard of claim 5, wherein the first brace member catch and the second brace member catch each comprise a hook.

8. The guard of claim 1, wherein the lower surface of the upper annular ring includes a first protrusion configured to be spaced a distance from the front or rear blade face of the first blade when the guard is mounted to the impeller and forming the first side of the first blade receiving groove, and a second protrusion configured to be spaced a distance from the front or rear blade face of the second blade when the guard is mounted to the impeller and forming the first side of the second blade receiving groove.

9. The guard of claim 8, wherein the first brace member inner side wall includes a first brace member extension forming a part of the vertical slot for receiving a portion of an inner edge of the first blade, and the second brace member inner side wall includes a second brace member extension forming a part of the vertical slot for receiving a portion of an inner edge of the second blade.

10. The guard of claim 8, wherein the first brace member has a first brace member bottom end including the catch for lockably receiving the portion of the lower edge of the first blade, and the second brace member has a second brace member bottom end including the catch for lockably receiving the portion of the lower edge of the second blade.

11. The guard of claim 8, wherein the first brace member catch and the second brace member catch each comprise a hook.

12. An impeller assembly comprising:
an impeller having at least a first blade and a second blade, each of the first and second blades having front and rear blade faces, an upper edge, an outer edge, an upper outer corner where the upper edge contacts the outer edge, a lower edge, and an inner edge; and
the guard of claim 2, mounted to the impeller.

13. An impeller assembly comprising:
an impeller having at least a first blade and a second blade, each of the first and second blades having front and rear blade faces, an upper edge, an outer edge, an upper outer corner where the upper edge contacts the outer edge, a lower edge, and an inner edge; and
the guard of claim 3, mounted to the impeller.

14. An impeller assembly comprising:
an impeller having at least a first blade and a second blade, each of the first and second blades having front and rear blade faces, an upper edge, an outer edge, an upper outer corner where the upper edge contacts the outer edge, a lower edge, and an inner edge; and
the guard of claim 5, mounted to the impeller.

15. An impeller assembly comprising:
an impeller having at least a first blade and a second blade, each of the first and second blades having front and rear blade faces, an upper edge, an outer edge, an upper outer corner where the upper edge contacts the outer edge, a lower edge, and an inner edge; and
the guard of claim 8, mounted to the impeller.

16. An impeller assembly comprising:
an impeller having at least a first blade and a second blade, each of the first and second blades having front and rear blade faces, an upper edge, an outer edge, an upper outer corner where the upper edge contacts the outer edge, a lower edge, and an inner edge; and
the guard of claim 1, mounted to the impeller.

17. An impeller system, comprising the impeller assembly of claim 16, wherein the impeller has a central opening, the impeller assembly further comprising a pin and a seat fitment.

18. A biocontainer system comprising: (a) a biocontainer comprising a closed container having an interior volume suitable for containing fluid, the container comprising a bottom wall, a top wall, at least one side wall, the side wall(s) being joined to the top wall and the bottom wall; and at least an inlet port, and a drain port, wherein the biocontainer further comprises: (b) the impeller system of claim 17, wherein the impeller is mounted to an inner surface of the bottom wall of the biocontainer.

19. A method for mounting the guard of claim 1 to an impeller, the method comprising:
   positioning the inner edges of the blades of the impeller in the vertical slots of the respective brace members;
   positioning the upper outer corners of the blades of the impeller in the respective blade receiving grooves; and
   positioning the lower edges of the blades of the impeller in the catches of the respective brace members.

20. A method for mounting the guard of claim 8 to an impeller, the method comprising:
   positioning the inner edges of the blades of the impeller in the vertical slots of the respective brace members;
   positioning the upper outer corners of the blades of the impeller in the respective blade receiving grooves; and
   positioning the lower edges of the blades of the impeller in the catches of the respective brace members.

* * * * *